United States Patent
Scivoletto

(10) Patent No.: US 6,248,763 B1
(45) Date of Patent: Jun. 19, 2001

(54) COMPOSITION FOR TREATING SKIN CONDITIONS

(76) Inventor: RoseMarie Scivoletto, 10249 El Paraiso Pl., Delray Beach, FL (US) 33446

( * ) Notice: Subject to any disclaimer, the term of this patent is extended or adjusted under 35 U.S.C. 154(b) by 0 days.

(21) Appl. No.: 09/414,849

(22) Filed: Oct. 12, 1999

Related U.S. Application Data

(63) Continuation-in-part of application No. 09/082,292, filed on May 19, 1998.

(51) Int. Cl.⁷ .................................................. A61K 31/44
(52) U.S. Cl. .............................. 514/356; 514/458; 514/2; 514/557; 514/738; 424/195.1
(58) Field of Search ..................................... 514/356, 458, 514/2, 557, 738; 424/195.1

(56) References Cited

U.S. PATENT DOCUMENTS

| | | |
|---|---|---|
| 3,729,568 | 4/1973 | Kligman . |
| 3,880,996 | 4/1975 | Fisher . |
| 3,906,108 | 9/1975 | Felty . |
| 3,912,666 | 10/1975 | Spitzer et al. . |
| 4,505,896 | 3/1985 | Bernstein . |
| 4,968,685 | 11/1990 | Grollier . |
| 5,157,036 | 10/1992 | Groller . |
| 5,240,945 | 8/1993 | Warshaw . |
| 5,468,492 | 11/1995 | Szaolki et al. . |

FOREIGN PATENT DOCUMENTS

| | | |
|---|---|---|
| 2210789 A1 | 6/1989 | (GB) . |
| 56964 A1 | 12/1982 | (IL) . |

OTHER PUBLICATIONS

CA 115:166437, Fed. Regist. (1991), 56(159), 41008–20 Aug. 16, 1991, abstract.

*Primary Examiner*—Rebecca Cook
(74) *Attorney, Agent, or Firm*—Oltman, Flynn & Kubler

(57) ABSTRACT

Compositions for skin treatment are disclosed and include nicotinamide, nicotinic acid, and nicotinic esters as active ingredients. The compositions are applied topically to the skin to treat skin conditions including acne, fine lines and age spots, itching and pain from insect bites, bee stings, fungi (including athletes foot and jock itch), flaking and/or scaly skin (including dandruff, seborrheic dermatitis, psoriasis and heat rash), and burns. Different compositions are presented for use as an acne treatment, a face and body wash, a dermatophyte (nail fungus) treatment. Still another is intended for use in makeup, and another in lipstick.

2 Claims, No Drawings

COMPOSITION FOR TREATING SKIN CONDITIONS

This application is a continuation-in-part of Ser. No. 09/082,292 filed May 19, 1998.

BACKGROUND OF THE INVENTION

1. Field of the Invention

The present invention relates generally to compositions for treating various skin conditions and, more particularly to a topically applied skin treatment composition including a nicotinic ester as an active ingredient.

2. Brief Description of the Prior Art

Various compositions containing nicotinic esters have been known and commonly used for inducing and stimulating hair growth. Examples of these can be found in the U.S. patents to Grollier, U.S. Pat. Nos. 5,157,036 and 4,968,685. In U.S. Pat. No. 5,468,492, Szaloki discloses a use of vitamin E nicotinate as a rubefacient to improve the circulation of the blood of the scalp. Other compositions containing methyl nicotinate have been proposed as an analgesic for the symptomatic relief of localized pain of musculo-skeletal etiology, as evidenced by the U.S. patent to Fisher, U.S. Pat. No. 3,880,996.

A product is available and sold under the trade name FINALGON, which is a topical rubefacient including nicotinic acid. The product is intended for use as a temporary relief from pain caused by muscular rheumatism and does not disclose use as a skin treatment.

A variety of published articles describe the effects and uses of nicotinic acid, nicotinamide and methyl nicotinate (Murrell, T., "The Cutaneous Reaction to Nicotinic Acid," *A.M.A. Archives of Dermatology,* 79:545–552, May, 1959, Shalita, A. R., "Topical nicotinamide compared with clindamycin gel in the treatment of inflammatory acne vulgaris," *International Journal of Dermatology,* 34(6): 434–7, June, 1995, and Remme, J. J., "Bullous pemphigold successfully controlled by tetracycline and nicotinamide," *British Journal of Dermatology,* 133(1): 88–90, July, 1995). None of these articles describe a use of the particular compositions of nicotinamide, its derivatives, nicotinic acid, its esters, or their derivatives as presented by this invention.

In U.S. Pat. Nos. 3,729,685 and 3,906,108 Kligman and Felty, respectively, describe a method of acne treatment which involves topical application of vitamin A to the skin. This method does not, however, include the use of vitamin B3, nicotinic acid or any salt thereof for acne treatment. One disadvantage of using vitamin A in skin treatment is the substantial skin irritation vitamin A causes. This irritation makes such treatment unpleasant and may even lead to an individual foregoing treatment altogether. Although a cream formulation of vitamin A may reduce the undesirable side effects, it does not do so entirely. This leaves an individual who applies the vitamin A treatment with irritated, stinging and itching skin.

The prior art does not provide for the topical application of nicotinamide, its derivatives, nicotinic acid, and nicotinic esters or their derivatives in the compositions presented herein. The present invention presents a spectrum of unique and novel formulas by which nicotinamides, nicotinic acids and nicotinic esters may be topically applied to the skin. Some of the formulas embody an original compilation of ingredients which include skin moisturizers, emollients, vitamin E, carriers and other beneficial elements. Some formulas are designed to dry quickly and clearly upon application. These formulas provide the user with a smooth and even skin tone without the greasy, sticky finish or irritation caused by many other skin care products. Further, these formulas are effective in treating a variety of disorders and skin conditions, including the removal of blackheads.

SUMMARY OF THE INVENTION

The present invention relates to a discovery that a nicotinic ester and particularly the compound methyl nicotinate, is highly beneficial when topically applied to treat skin conditions. More particularly, when combined with a skin moisturizer, a suitable carrier, an emollient (e.g. glycerol or glycerin), vitamin E and other elements and excipients, methyl nicotinate, and nicotinic acid have surprising efficacy in treating various skin conditions including: acne blemishes; acne pimples, blackheads and whiteheads; psoriasis; seborrheic dermatitis, or dandruff; large pores, fine lines and age spots; stretch marks; cellulite; itching; pain and itching from insect bites and stings; fungi; varicose veins; flaking and scaly skin; burns (including sunburn); bedsores and black and blue marks.

In addition to those listed heretofore, minor amounts of other additives may optionally be present. This would include an ingredient effective in treating dermatophyte fungi.

The invention also encompasses a method of using the composition to treat various skin conditions or other disorders. This method generally includes patting the composition on one's palm or an applicator, such as a cosmetic pad or cotton. The composition is then topically applied to the skin or other affected area such as a fingernail or toenail. The application may also include, in the case of using the composition as a body or facial wash, applying the composition to one's skin then rinsing it away with water.

DESCRIPTION OF THE PREFERRED EMBODIMENTS

The disclosed embodiments of the present invention display certain preferred compositions but are not intended to limit the scope of the invention. As will be obvious to those skilled in the art, multiple variations and modifications may be made without departing from the scope of the invention.

In the following preferred embodiments, the active ingredient listed is methyl nicotinate. The composition might otherwise utilize nicotinamides, derivatives thereof, nicotinic acids, nicotinic esters or derivatives thereof as an active ingredient.

In a preferred embodiment intended to treat acne, psoriasis, seborrheic dermatitis or dandruff and dermatophyte fungi, the composition has the following ingredients:

| | |
|---|---|
| Methyl nicotinate | 0.01 to 1% |
| Niacin | 0.01 to 1% |
| Glycolic Acid | 0.01 to 20% |
| Aloe vera gel | 35 to 45% |
| Glycerin | 0.8 to 1.8% |
| DMDM hydantoin | 0.02 to 0.25% |
| Tetrasodium EDTA | 0.05 to 0.15% |
| Vitamin E | 0.01 to 0.1% |
| Polysorbate-20 | 0.5 to 1.0% |
| Silk amino acids | 0.01 to 0.1% |
| Hydrolyzed collagen | 0.01 to 0.1% | and distilled, deionized or demineralized water to bring the total weight concentration to 100%. This composition may also include any combination in whole or in part of resorcinol, sulfur, resorcinol monoacetate, salicylic acid and witch hazel.

With or without glycolic acid, this composition is also used as a makeup toner (before applying makeup or lipstick) for longer and fresher lasting makeup and lipstick all day, and balancing the dry or oily and combination skin, enhancing a glow to makeup and lipstick. Also, this composition is used before applying sunblock with S.P.F. at 2% to 30%+ for lasting effect of the sun block or sun screen. It is also used as a pre-shave lotion and can be used in shaving lotion. It is also used for large pores, fine lines, age spots, cellulite, itching, insect bites and stings, flaking and scaly skin, bedsores and black and blue marks.

The preferred method of using the composition for acne, psoriasis, dermatits or dandruff and dermatophyte fungi is to apply it directly to the skin or other affected area without the glycolic acid. To promote vasodilation, this may be done using the palm of the hands or an applicator such as a cotton or a cosmetic pad. The same composition with glycolic acid is then applied on top of the first composition as a spot treatment on the firm elevation of the pimple or whitehead, dead skin of psoriasis and fungi where bacteria breeds. It is applied twice a day for 2 to 3 days to the affected area. The glycolic acid in the second composition acts as an exfoliant, and it peels away the unwanted material. It is removed to stop the peeling, and the first composition is applied to continue vasodilation to improve the supply of blood to the affected cells.

Persons using the composition have reported the clearing up of any blemishes as well as an inhibitory effect wherein new blemishes or breakouts are prevented from forming. The composition's users relate marked improvements in their skin's texture and acne condition, psoriasis and fungus. Other users have stated that the product improved their acne condition as well as the general color and clarity of their skin within a relatively short period of use, two days.

An ingredient or combination thereof intended to treat dermatophyte fungi may be included in the composition. This ingredient may include 3% chiquinol, 1% haloprogin, 2% miconazole nitrate, 10% providone iodine, 1% tolnafate, or 10 to 25% undecylenic acid or a salt thereof. The undecylenate ingredient may include calcium undecylenate, copper undecylenate, or zinc undecylenate or a combination thereof. The weight concentrations of these ingredients may also vary according to different formulations of the composition.

Some users of the fungus treatment have reported a 95% improvement in their fungus condition. Others have indicated that the composition relieved what had been a disabling finger pain caused by nail fungus to a point of virtual painlessness. Another individual indicated that use of the composition to treat nail fungus has led to increased nail growth and generally harder nails.

In another embodiment of the composition, intended as a general treatment and daily cleanser for face, body and scalp wash and foot bath, the following ingredients are employed:

| | |
|---|---|
| Methyl nicotinate | 0.01 to 20% |
| Niacin | 0.01 to 1% |
| Aloe vera gel | 60 to 70% |
| Ammonium lauryl sulfate | 20 to 28% |
| Cocamidopropyl betaine | 3 to 5% |
| Lauramide DEA | 3 to 5% |
| Glycerin | 0.8 to 2.5% |

-continued

| | |
|---|---|
| Methylparaben | 0.8 to 1.2% |
| Propylparaben | 0.8 to 1.2% |
| Propylene glycol | 0.8 to 1.2% |
| Imidazolidinyl urea | 0.8 to 1.2% |
| Guanine | 0.1 to 0.15% |
| Tea-lauryl sulfate | 0.1 to 0.15% |
| Isopropyl alcohol | 0.1 to 0.15% |
| Methylcellulose | 0.1 to 0.15% |
| Vitamin E | 0.01 to 0.1% |
| Silk amino acids | 0.01 to 0.1% |
| Hydrolyzed collagen | 0.01 to 0.1% |
| Chamomile | 0.01 to 0.1% | and distilled, deionized or demineralized water to bring the total weight concentration to 100%. This composition may also be used on dogs with or without a sulfur additive from 1 to 8%.

This composition would commonly be used by applying the composition to the user's skin, then rinsing it away with water.

This composition is intended for use in treating dry or oily skin, or skin that is a combination of dry and oily, as well as fine lines, enlarged pores, chapped lips, and as an anti-itch formula, on insect stings and bites.

Persons using this composition have reported that it has kept their face from getting oily, prevented breakouts, and reduces fine lines on the face. The composition is said to leave a tingling sensation with increased warmth and has been very useful in treatment of itching sensations caused by rashes and insect bites. The composition stimulates the oil glands dissipating the oil so blood can get to the cells. The composition is also useful in treating other skin conditions such as psoriasis, athletes foot, eczema, hives or other allergic reactions and associated symptoms that accompany these conditions such as itching. The composition removes dead skin and penetrates the pores.

In addition to treating human skin disorders and or conditions, the various embodiments of the composition presented may be used to treat dogs, cats, horses, and other animals. Two individuals reported use of the composition on a dog having itching problems which had scratched itself to the point of having large irritated bare spots and rashes which sometimes bled. The composition alleviated the dog's discomfort to the point where it no longer scratched and its hair grew back.

Another embodiment of the composition, intended to be applied and left on, includes following ingredients:

| | |
|---|---|
| Methyl nicotinate | 0.01 to 8% |
| Niacin | 0.01 to 1% |
| Glycerin | 0.8 to 2.5% |
| Isopropyl palmitate | 1 to 15% |
| Myristyl myristate | 1 to 15% |
| Glyceryl ricinoleate | 1 to 15% |
| Octyldodexanol | 1 to 15% |
| Microcrystalline wax | 1 to 10% |
| Acetylated lanolin | 1 to 10% |
| Candelilla wax | 1 to 10% |
| Carnauba | 1 to 10% |
| Isopropyl lanolate | 1 to 15% |
| Cetyl alcohol | 1 to 15% |
| Mineral oil | 1 to 15%. |

This composition may be used in lipstick.

Another embodiment of the composition is intended for use with makeup and may be used in makeup. This embodiment includes the following ingredients:

| | |
|---|---|
| Methyl nicotinate | 0.01 to 8% |
| Niacin | 0.01 to 1% |
| Glycerin | 0.8 to 2.5% |
| Octylmethothoxycinnamate | 0.8 to 2% |
| Benzophenone-3 | 0.8 to 2% |
| Propylene glycol | 0.8 to 2% |
| Soy lecithin | 0.08 to 2% |
| Glyceryl stearate | 0.08 to 2% |
| Peg-100 stearate | 0.08 to 2% |
| Cetearyl alcohol | 0.1 to .15% |
| Ceteareth-20 | 0.08 to 2% |
| Sodium PCA | 1 to 10% |
| Tocopheryl linoleate | 1 to 10% |
| Tocopheryl acetate | 1 to 10% |
| Methylparaben | 0.8 to 2% |
| Ethylparaben | 0.8 to 2% |
| Propylparaben | 0.8 to 2% |
| DMDM hydantoin | 0.8 to 2% |

This composition would be primarily used in facial makeup along with other dyes, perfumes, colorings, and additives. A similar composition might be used in sun block and sun screen with or without S.P.F. 2% to 30%+

While the invention has been described and disclosed in certain embodiments, the scope of the invention is not intended to be, nor should it be deemed to be, limited thereby and such other modifications as may be suggested by the teachings herein are particularly reserved especially as they fall within the breadth and scope of the claims here appended.

I claim:

1. A method of treating psoriasis affected areas of the skin comprising:

topically applying to said affected areas twice a day an effective amount of a composition comprising by weight, 0.01 to 1.0% methyl nicotinate;

by weight, niacin 0.01 to 1%;

by weight, 35 to 45% aloe vera gel;

by weight, 0.8 to 1.8% glycerin;

by weight, 0.02 to 0.25% DMDM hydantoin;

by weight, 0.05 to 0.15% tetrasodium EDTA;

by weight, 0.01 to 0.1% Vitamin E by weight, 0.5 to 1.0% polysorbate-20;

by weight, 0.01 to 0.1% silk amino acids;

by weight, 0.01 to 0.1% hydrolyzed collagen; and, water.

2. A method of treating psoriasis affected areas of the skin comprising:

topically applying to said affected areas twice a day for two to three days an effective amount of a composition comprising by weight, 0.01 to 1.0% methyl nicotinate;

by weight, niacin 0.01 to 1%;

by weight 35 to 45% aloe vera gel;

by weight, 0.8 to 1.8% glycerin;

by weight, 0.02 to 0.25% DMDM hydantoin;

by weight, 0.05 to 0.15% tetrasodium EDTA;

by weight, 0.01 to 0.1% Vitamin E by weight, 0.5 to 1.0% polysorbate-20;

by weight, 0.01 to 0.1% silk amino acids;

by weight, 0.01 to 0.1% hydrolyzed collagen;

by weight, 0.01 to 20% of a peeling agent, glycolic acid; and, water.

* * * * *